(12) United States Patent
Fox

(10) Patent No.: US 11,944,352 B2
(45) Date of Patent: Apr. 2, 2024

(54) EXTRACORPOREAL BONE COMPRESSING LINK AND APPARATUS AND METHOD USING SAME

(71) Applicant: William Casey Fox, Pipe Creek, TX (US)

(72) Inventor: William Casey Fox, Pipe Creek, TX (US)

( * ) Notice: Subject to any disclaimer, the term of this patent is extended or adjusted under 35 U.S.C. 154(b) by 275 days.

(21) Appl. No.: 17/334,540

(22) Filed: May 28, 2021

(65) Prior Publication Data

US 2022/0378478 A1  Dec. 1, 2022

(51) Int. Cl.
| | | |
|---|---|---|
| A61B 17/66 | (2006.01) | |
| A61B 17/00 | (2006.01) | |
| A61B 17/56 | (2006.01) | |
| A61B 17/60 | (2006.01) | |

(52) U.S. Cl.
CPC .... *A61B 17/66* (2013.01); *A61B 2017/00867* (2013.01); *A61B 2017/564* (2013.01); *A61B 2017/606* (2013.01)

(58) Field of Classification Search
CPC ..... A61B 17/60; A61B 17/64; A61B 17/6425; A61B 17/6458; A61B 17/66; A61B 2017/564; A61B 2017/606; A61B 2017/681
See application file for complete search history.

(56) References Cited

U.S. PATENT DOCUMENTS

| | | | | |
|---|---|---|---|---|
| 5,074,865 A | * | 12/1991 | Fahmy | A61B 17/6425 606/57 |
| 10,123,831 B2 | * | 11/2018 | Gephart | A61B 17/808 |
| 10,448,979 B2 | | 10/2019 | Fox | |
| 10,537,370 B2 | | 1/2020 | Fox | |
| 2006/0058796 A1 | * | 3/2006 | Hartdegen | A61B 17/8014 606/291 |
| 2008/0195095 A1 | | 8/2008 | Renard et al. | |
| 2008/0221571 A1 | | 9/2008 | Daluiski et al. | |
| 2010/0280516 A1 | * | 11/2010 | Taylor | A61B 17/62 606/57 |
| 2011/0034924 A1 | * | 2/2011 | Tan | A61B 17/66 606/59 |
| 2011/0264149 A1 | | 10/2011 | Pappalardo et al. | |
| 2012/0029517 A1 | | 2/2012 | Tan | |

(Continued)

FOREIGN PATENT DOCUMENTS

| | | | | |
|---|---|---|---|---|
| CN | 112370156 A | * | 2/2021 | ............ A61B 17/66 |
| CN | 112370156 A | | 2/2021 | |

OTHER PUBLICATIONS

International Searching Authority, International Search Report and Written Opinion for PCT/US2022/031309, dated Sep. 15, 2022; 16 pages.

(Continued)

*Primary Examiner* — Eduardo C Robert
*Assistant Examiner* — Michelle C Eckman
(74) *Attorney, Agent, or Firm* — Dickinson Wright PLLC; Ross Spencer Garsson

(57) ABSTRACT

An extracorporeal bone compressing link and apparatus and method using same. Active devices that incorporate the extracorporeal bone compressing link can transport and (Continued)

compress bone through external means by acting on conventional bone fasteners including but not limited pins or wires that penetrate through the skin and fixate into bone.

25 Claims, 31 Drawing Sheets

(56) References Cited

U.S. PATENT DOCUMENTS

| | | |
|---|---|---|
| 2012/0226277 A1 | 9/2012 | Tan et al. |
| 2013/0046347 A1 | 2/2013 | Cheng et al. |
| 2013/0116692 A1 | 5/2013 | Daluiski et al. |
| 2014/0257420 A1 | 9/2014 | Fox |
| 2015/0100057 A1 | 4/2015 | Zgonis et al. |
| 2015/0257801 A1* | 9/2015 | Palmer ............... A61B 17/8085 606/281 |
| 2015/0366587 A1 | 12/2015 | Van Dyke et al. |
| 2016/0000466 A1 | 1/2016 | Chang |
| 2016/0235444 A1 | 8/2016 | Crozet et al. |
| 2017/0281157 A1 | 10/2017 | Hartdegen et al. |
| 2020/0375628 A1* | 12/2020 | Foo ..................... A61B 17/6425 |
| 2022/0226028 A1* | 7/2022 | Dayton ................ A61B 17/863 |

OTHER PUBLICATIONS

Asche, G., et al., "Hoffman II Micro External Fixation System", Styker Osteosynthesis, 2009, www.osteosynthesis.stryker.com; 20 pages.

Depuy Synthes, "Mini External Fixator", Johnson & Johnson Medical Devices Companies; 2021; (https://www.injmedicaldevices.com/en-US); 3 pages.

Depuy Synthes, "Stabilize the Phalanges and Metacarpals: Mini External Fixator", Surgical Technique, 2021 11 pages.

Ichihara, S., et al. "Open Reduction and Intrafagmentary Compression Fixation with External Fixator (the Ichi-Fixator) Treatment of Distal Phalangeal Nonunion", Hindawi Case Reports in Orthopedics, vol. 2020, Article ID 8878002, 4 pages; https://doi.org/10.1155/2020/8878002.

Virak Ortho, "Digi Fix: A Unique Versatile Small Bone Mini Ex-Fix", 2020 (https://www.virakortho.com/clinical-overview/); 2 pages.

* cited by examiner

EXTRACORPOREAL BONE COMPRESSING LINK AND APPARATUS AND METHOD USING SAME

TECHNICAL FIELD

The present invention relates to active devices that transport and compress bone through external means by acting on conventional bone fasteners including but not limited pins or wires that penetrate through the skin and fixate into bone.

BACKGROUND

Bone fixating devices are generally implants such as plates, screws, rods and staples that reside within the body. The most advanced of these technologies involve shape changing staples of nitinol. These devices use nitinol's memory and super elastic properties to return to a pre-programmed shape which can pull together and compress bone. They are often used to bridge fractures or joints to be fused so that they hold the healing bone interface in contact and provide compression during bone healing.

Prior to the use of shape changing implants static plates and staples were used. These devices often lost fixation and could not store mechanical elastic energy to act like a spring to compress the healing bone. Before plates, screws and staples, skin penetrating pins and wires were often the only method of providing fixation to bone while healing. These devices are still used today due to their low cost, ease of use, minimally invasive nature but suffer from the inability to provide sufficient fixation and cannot reduce and compress bone while healing.

Yet, the use of shape changing implants still involve invasive techniques where the surgeon operates under the skin. The use of shape changing materials as a means to heal bones or for use in bone fixation, such as those described in patents of the Applicant (i.e., Fox '979 patent; Fox '370 patent), utilize implants that change shape only after being implanted under the skin. Thus, even following the use of shape changing implants, there still remains a partially invasive nature of the implant.

The prior art is without a solution to combine the ease and minimally invasive nature of percutaneous wires and pins with an extracorporeal link that act on these pins and wires to create a moment and apply forces which causes bone movement and compression deep within the body.

The subject invention accomplishes that goal while providing (1) a guide to place the pins into bone, (2) adjustability of the deep bone applied force, and (3) an instrument that retains the shape of the link until released and during removal re-aligns the link so that it can be slid off the pins or wires. Once pinned and released the link changes shape to cause the tip of the pin or wire to move and apply forces to the bone in which the pin or wire is located.

SUMMARY OF THE INVENTION

Representative embodiments set forth herein disclose a shape changing link.

In some embodiments, the link acts on pins or wires that are fixed in bone on a first end, penetrate the skin and are acted on by the link on a second end to apply forces to bones. In certain embodiments, the link is external to the body.

The link causes bone transport and creates bone-to-bone compression by pulling or imposing inward directed mechanical moments on the portion of the wires or pins that are outside of the body. Moments are applied by angular shape change of the link. Pulling or pushing forces are created by the shortening or lengthening of the link. In some embodiments, the link can distract bone by lengthening or imposing outward moments that separate bones.

Holes in the link receive and during elastic recovery of the link impart forces to the wires or pins. The portion of the link with wire holes changes the angle of the holes relative to the wires to impart forces to and creates mechanical moments in the wire. The wire hole portion of the link, defined herein as a pin tower, thickness can be used to adjust the magnitude of twisting torque imparted to the wire when the hole changes angle. This applied torque causes the distant tip of the wire to move or apply forces if the wire tip is constrained.

The link has a first and second shape. The first shape is retained by an instrument. In this shape the holes are aligned so that when wires or pins are passed through the link they are of a known relative orientation (e.g., parallel, divergent, convergent), can penetrate the skin and be advanced so that the tip or the wire or pin is implanted in bone. The second shape transitions to a first shape when the instrument releases the link. The instrument allows the surgeon to position the link above the skin and insert the pin or wire through the link, skin and into bone. Once a plurality of pins are inserted through the link and into bone the instrument is operated to release the link so that the link moves toward its first shape.

As the link changes to its first shape the holes try to change alignment with the pins or wires. This alignment change pulls, pushes or imparts moments to the pin or wire to move the end of the pin in bone or impart forces to compress bone segments.

The force applied to bone by the pins, wires and link assembly can be changed through the design of the link or distance of the link above bone along the length of the wire or pin. Since the force imparted to bone is a function of the length of the wire or pin at the point of mechanical moment application the surgeon will have operative control of the amount of force to be applied.

The link can be fabricated from metals or plastics that exhibit elastic behavior. This elasticity stores mechanical energy for dynamic and long-term effect on the fixated bone. Plastic or metal links can be fabricated by machining, additive manufacturing, extruding, casting or molding. Since the link is not body contacting it may be fabricated from materials that are not generally considered biocompatible which might broaden the window of performance of the system and reduce cost.

In surgical use the link holes provide guides for the pin or wire placement. The instrument holding the link in the first shape facilitates this operative technique by allowing the surgeon to visualize the surgical site, the location of the pins, the height of the link above the skin and then without additional steps in the procedure releases the link to mechanically act on its pins and wires to create bone compression.

In general, in one embodiment, the invention features an extracorporeal link for connecting percutaneous bone fasteners that includes an element. The element includes a plurality of transverse holes. The plurality of transverse holes are located about the element. Each transverse hole in the plurality of transverse holes is capable of allowing a bone fastener to pass through the transverse hole in the plurality of transverse holes to secure to one or more bone segments. The element is configured in a first configuration. The element is operable for being held under force in a second configuration. The element is operable to move toward the first configuration after being released from the force. The movement toward the first configuration is capable of applying moments and forces to the bone fastener. The moments and forces capable of being applied to the bone fastener are operable to act through the skin to transport and compress the one or more bone segments.

Implementations of the invention can include one or more of the following features:

The extracorporeal link can be operatively positioned in a plurality of bone fragments.

The material can include one or more cross-sectional geometries.

Each transverse hole in the plurality of transverse holes can be capable of guiding the bone fastener. The bone fastener can be positioned through the extracorporeal link, skin, and the bone.

The movement toward the first configuration after being released from the force can operatively position the bone fastener to enter the bone at a desired direction.

The extracorporeal link can be held by a restraining instrument in a sterile kit.

The restraining instrument can include a restrainer selected from a group consisting of pliers, power screws, sliding platens, and pin tower tubes.

The sterile kit can include the extracorporeal link, the restraining instrument, a plurality of bone fasteners, and a plurality of pin tower tubes.

The extracorporeal link can be operatively connected to a protective cover.

The protective cover can include a material selected from a group consisting of plastic, rubber, latex, or combinations thereof.

In general, in another embodiment, the invention features an apparatus for percutaneous bone fastening. The apparatus includes an extracorporeal link. The extracorporeal link includes a plurality of transverse holes. The plurality of transverse holes are located about the extracorporeal link. Each transverse hole in the plurality of transverse holes is capable of allowing a bone fastener to pass through the transverse hole in the plurality of transverse holes to secure to one or more bone segments. The extracorporeal link is capable of being configured in a first configuration. The extracorporeal link is configured in a second configuration. The apparatus further includes a restraining instrument. The extracorporeal link is operatively positioned by the restraining instrument. The operative positioning of the instrument holds the extracorporeal link in the second configuration. When released from the operative positioning of the restraining instrument, the extracorporeal link operatively moves toward the first configuration.

Implementations of the invention can include one or more of the following features:

The movement toward the first configuration can be capable of applying moments and forces to the bone fastener.

The moments and forces capable of being applied to the bone fastener can be operable to act through the skin to transport and compress the one or more bone segments.

The restraining instrument can include a restrainer selected from a group consisting of pliers, power screws, sliding platens, and pin tower tubes.

In general, in another embodiment, the invention features a method for using an extracorporeal link for connecting percutaneous bone fasteners. The method includes selecting an element. The element includes a plurality of transverse holes. The plurality of transverse holes are located about the element. Each transverse hole in the plurality of transverse holes is capable of allowing a bone fastener to pass through the transverse hole in the plurality of transverse holes to secure to one or more bone segments. The element is configured in a first configuration. The method further includes restraining the element in a second configuration. The element is restrained using external force. The method further includes positioning the element near, but not proximate to, one or more bone segments. The method further includes passing a plurality of bone fasteners through the plurality of transverse holes. The method further includes releasing the element from the external force. Responsive to releasing the element from the external force, the element moves toward the first configuration. The movement toward the first configuration applies moments and forces to the plurality of bone fasteners. The moments and forces being applied to the plurality of bone fasteners act through the skin to transport and compress the one or more bone segments.

Implementations of the invention can include one or more of the following features:

The positioning of the element can adjust the moments and forces being applied to the plurality of bone fasteners.

The external force can be applied by a restraining instrument.

The restraining instrument can include a restrainer selected from a group consisting of pliers, power screws, sliding platens, and pin tower tubes.

In general, in another embodiment, the invention features a method for making an extracorporeal link for connecting percutaneous bone fasteners. The method include selecting a material. The material includes a memory-shape metal. The material is in a first configuration. The method further includes cooling the material. The material is operable for being reconfigured to a second configuration. The material is capable of remaining in the second configuration absent an external force. The material is capable of moving toward the first configuration at an elevated temperature. The method further includes, responsive to cooling the material, reconfiguring the material into the second configuration. The method further includes responsive to reconfiguring the material, restraining the material in a restraining instrument. The restraining instrument restrains the material in the second configuration at the elevated temperature.

Implementations of the invention can include the following feature:

The material can be nitinol.

BRIEF DESCRIPTION OF THE DRAWINGS

Other advantages of the present invention will be apparent from the following detailed description of the invention in conjunction with embodiments as illustrated in the accompanying drawings, in which.

LIST OF REFERENCE NUMERALS

Figure 1:
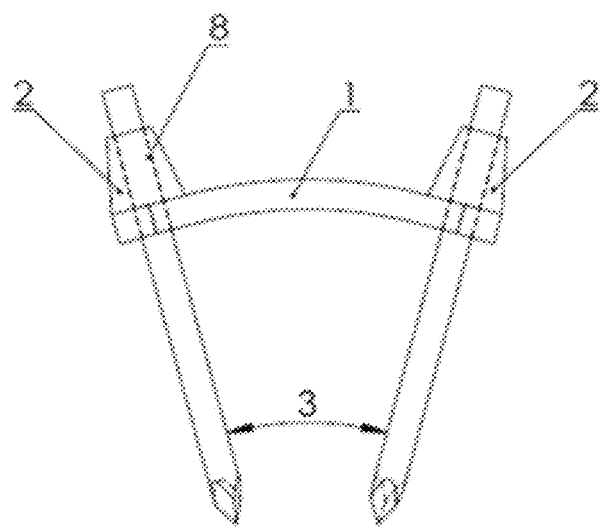
FIG. 1 depicts a perspective view of a link in the unstressed first shape with wires or pins.

1 Link member
2 Link integral pin towers
3 K-wires, pins or other skin penetrating bone fasteners
4 Moment (M) created by link shape change
5 Force ($F_S$) of link shortening
6 Height (H) of link above bone
7 Force ($F_B$) acting on bone
8 Pin tower hole to receive bone fastener
9 Link member in its straight stressed second shape
10 K-wire just prior to insertion
11 K-wire fully inserted
12 K-wire being inserted
13 Link member designed to not change shape
14 Fulcrum of plier
15 Plier levers
16 Plier Link compression head
17 Link compression head
18 Link threaded power screw actuator
19 Rotating handle
20 Stationary handle
21 Link instrument guide handle
22 Link instrument drill guide and pin tower retention tube
23 Link cylindrical pin tower
24 Link in second stressed state
25 Link release button prior to release
26 Link release button at the point of release
27 Link after release in its relaxed initial state shown acting on the k-wires
28 Link instrument fixed platen
29 Link instrument movable release platen
30 Plier handle fixed
31 Plier handle movable
32 Link instrument platen mechanism
33 Tubular Link first shape
34 Tubular Link second stressed shape
35 Pin tower holes
36 Link holder inserts
37 Tubular Link plier fulcrum
38 Tubular Link plier handle
39 Link plate in stressed second shape
40 Link plate in first shape

DETAILED DESCRIPTION OF THE INVENTION

The present invention relates to a shape changing link that is used external to the body to act on bone fasteners.

In particular, in certain embodiments, the shape changing link that is used external to the body to act on bone fasteners includes, but is not limited to, wires and pins 3 that penetrate the skin and fixate bone. The link has a first unstressed shape 1 and is strained and held by an instrument to achieve a shape recoverable stressed shape 9.

Figure 2:
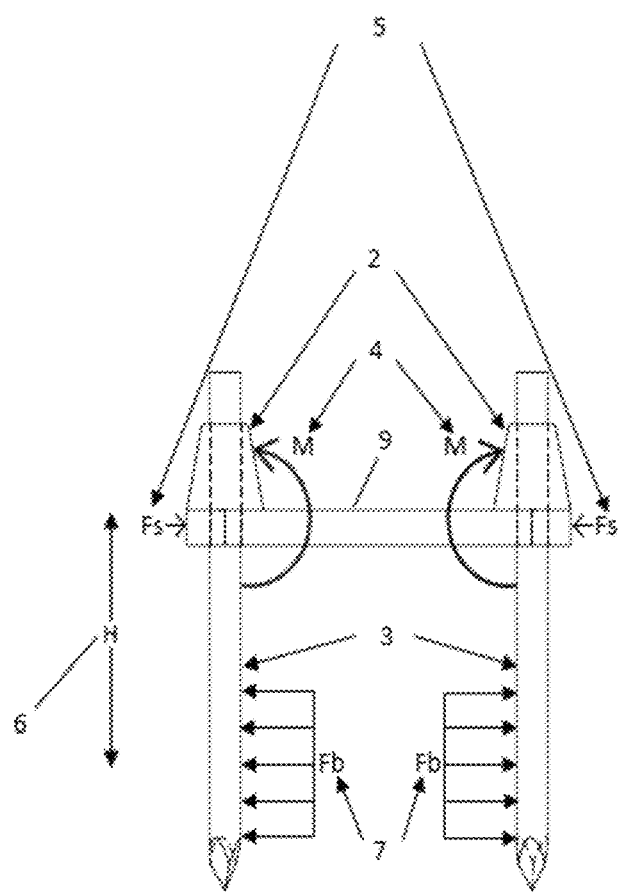
FIG. 2 depicts a mechanical free body diagram of a link showing forces and moments acting on wires or pins.
Figure 3:
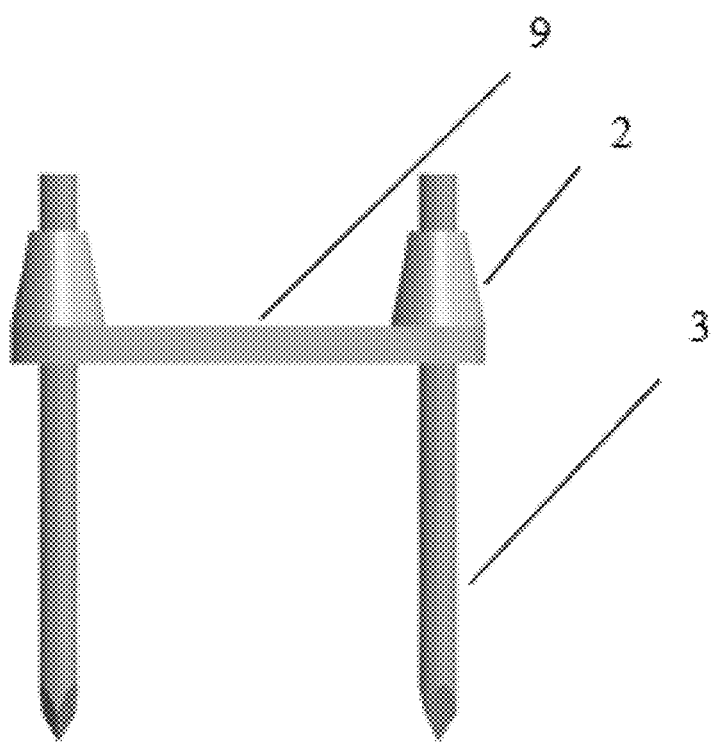
FIG. 3 depicts a perspective front view of a link in second shape as it would be held by the instrument.
Figure 4:
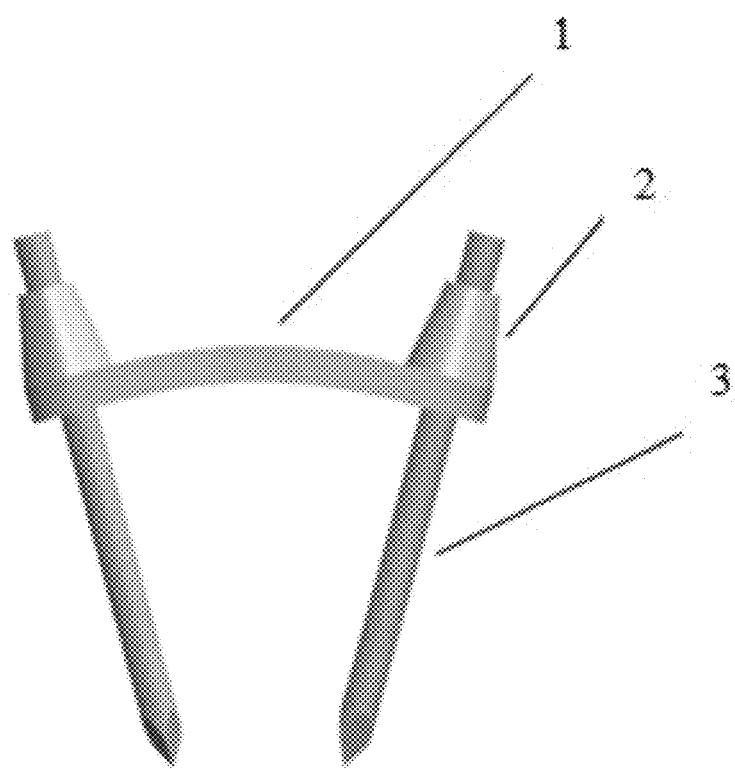
FIG. 4 depicts a perspective front view of a link in first shape after release by the instrument.
Figure 5:
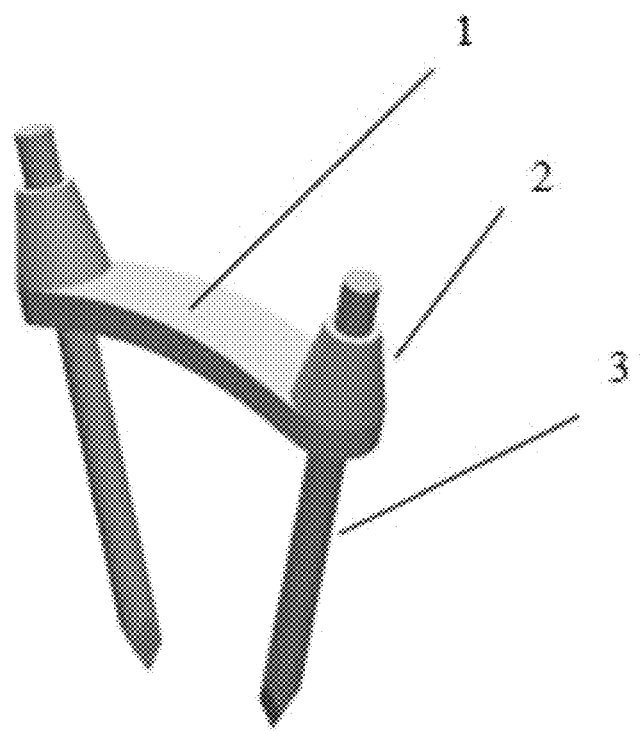
FIG. 5 depicts an orthogonal view of a link.

When fabricated, the link is formed in the first unstressed shape 1, as displayed in FIG. 1. When instrument held, the link is in the stressed recoverable second shape 9, as displayed in FIG. 2. When held wire, pin or other fasteners 3 can be inserted through the holes 8 in the link, through skin and into bone. When released from the instrument the link acts to recover its first unstressed shape 1 thus acting to apply moments (M) 4 and forces ($F_S$) 5 on the k-wire or pin 3, as displayed in FIG. 2. The link acting on the k-wire or pin 3 causes the tips to move or if restrained by bone, forces ($F_B$) to be applied to bone 7, as shown in FIG. 2.

Height (H) 6 is the height of the link above bone when the link is released from the stressed recoverable second shape 9 toward the first unstressed shape 1. Since the fasteners 3 can be inserted through holes 8 in the link, height (H) 6 is adjustable. As the height of height (H) 6 decreases, the magnitude of the moments (M) 4, a property of the link, remains constant and forces ($F_S$) 5 increase. Thus, by setting the height (H) 6 at a pre-determined distance ($F_S$) 5 can be controlled to a pre-determined amounts for any given link. The magnitudes of moments (M) 4 can be set through the design of the link.

Generally, the fixation requirements are to stabilize and compress healing bone. On occasion the clinical need is to distract the bones and the link can be fabricated to either compress or distract. The link 1 can have a plurality of k-wires or pins 3 and act on the pins 3 in a plurality of directions. The link 1 can accept its pins or wires 3 in a plurality of shape changing holes 8 to fixate a multitude of bones, bone fragments and bone anatomies.

The ability to program the link shape change to act on bone through the skin provides an endless number of link geometries acting on a plurality of wires and pins to program the bone movement or compression to meet unique clinical needs. In certain embodiments, the pins, wires and screws can be pulled together in a linear fashion, to a central location or some other location driven by the link design and pin placement strategy.

Due to the link being external to the body and not skin contacting the material for the link can be most any material that exhibits elastic behavior. In some embodiments, the materials include, but are not limited to, nitinol, titanium, stainless steel, polyethylene, polypropylene, polyester ether ketone, Teflon® and nylon. This convenience allows a manufacturing cost reduction, a wide range of elastic properties, designs and bone compressing options.

In clinical use, the link is held in a surgical instrument in a second shape. This held shape is strained from its initial relaxed shape, has the link pin holes aligned with one another and with the desired bony location of the pin. The instrument held link act as a guide for the placement of the pins or wires. The surgeon will introduce each pin or wire through the link, skin and into bone. X-ray visualization enhances planning and placement of the link and its fixation pins or wires. Once all pins or wires are placed the surgeon releases the restraining instrument allowing the link to change shape, act on the pins or wires and compress the bony structures.

The instrument with link allows the surgeon to vary the distance of the link above the skin and provides the surgeon the ability to adjust the bone fixation force by releasing the link at different locations on the pins. This change in the point of moment application of the link on the pin changes the force applied to bone. The shorter the distance between the link and the bone the higher force imparted to the bone by the moment created by the link.

The pins, wires or other bone fastener, such as a screw can be used with the link. If a screw the portion acted on by the link is unthreaded or threaded. If unthreaded the link height can be adjusted in the same manner as if a pin. If threaded the link may have threads and as the screw is advanced bone is fixated and the link and screw are fastened to each other in an adjustable manner.

The link at the point of penetration of a pin, wire or screw can be capped to cover the exposed end of the pin, wire or screw. This avoids any catching of the externalized fixation on things in the environment such as bandages, clothing, furniture etc.

When bone healing has occurred the link can be removed. To remove the link the instrument is re-applied to the link and activated to return the link to its strained second shape. This re-aligns the pin holes with the pins, removes any shortening or lengthening force and allows the link to be slid off the pins or wires. Once the link is removed the wires or pins are removed by turning and pulling on the pins with a driver. Once the pins or wires are removed the small skin penetration holes heal with only a bandage covering.

Due to the simple and minimally invasive nature of this invention failure to obtain the desired bone fusion result is not catastrophic for the link and wire placement trauma is very low and its use does not preclude a more invasive device and fixation techniques at a later date.

To provide for a number of link shapes, pin hole placements and pin types the instrument that strains the link may by fabricated with multi-link compatible designs or replaceable heads specific to each link design. In this manner a single instrument that acts to strain the link can be used for many link designs.

The instrument must deform the link into its stressed second shape and retain it in this shape during use and storage. It may compress, stretch or align the pin towers of the link. The instrument's operation can be based on mechanical designs including but not limited to single or multiple action pliers, power screw driven compressing devices (vice, clamp, pivoting levers for example), sliding or rotating mechanism that releases the link into the stressed second shape (FIGS. 18-23, and FIGS. 25-29).

The simple and disposable nature of the instruments, link, pins and wires may allow the link system to be fully contained in a sterile kit. This minimizes disease transmission, provides convenience, assures all components are available and speeds the operative procedure. The common availability of sterile k-wires and pins and the external nature of the link and its instrument can allow this type of system to be used with sterile pins and wires and a non-sterile link and instrument.

The link can take many designs and a plurality of pins or wires. Accordingly, in certain embodiments, the link may have a plurality of pin tower holes distributed on the link in a fashion so that their orientation includes but is not limited to triangular, square, linear, or circular.

In some embodiments, the link can be designed to change shape in a plurality of directions so as to pull together, push apart, pull in a single direction or a plurality of directions. In such an embodiment, this allows multiple pins in a single bone or in multiple bones to meet variable clinical requirements for fixation. Thus, in some embodiments, the pin orientation relative to each other includes but is not limited to parallel, divergent or convergent when being placed through the link while it is being held in its stressed second shape.

Figure 6:
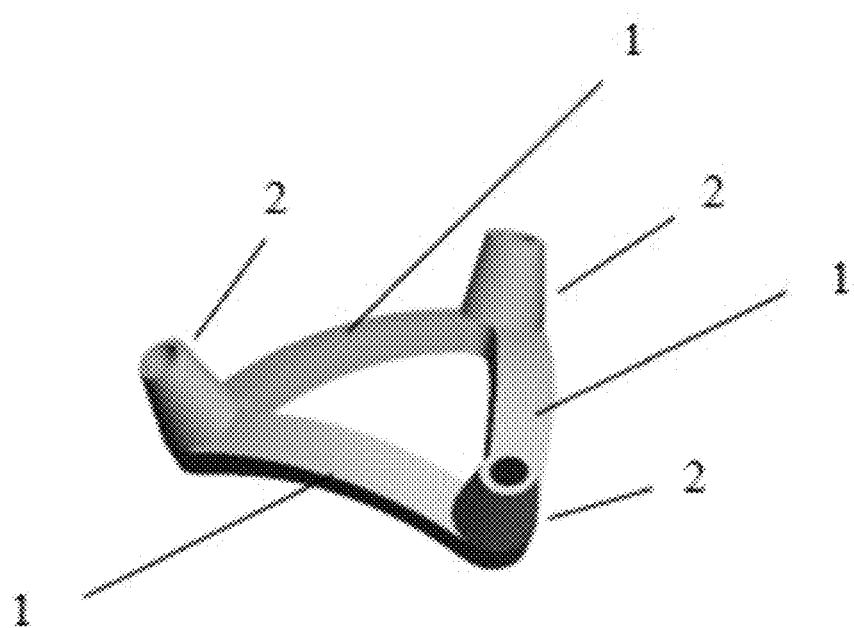
FIG. 6 depicts a perspective view of a link with three sides and fastener holes in first shape.
Figure 7:
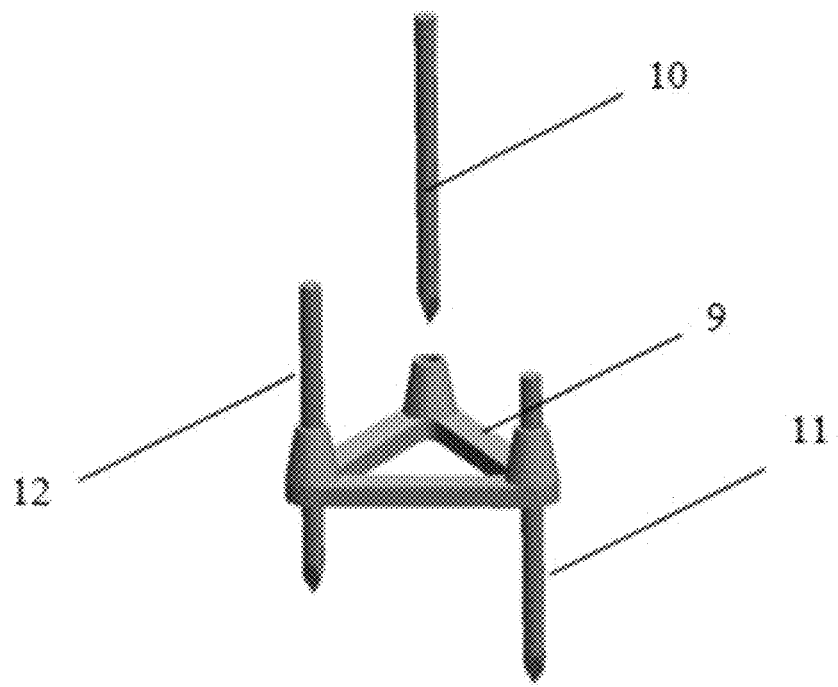
FIG. 7 depicts a perspective view of a link with three sides as held in its second shape with bone fastening wires inserted and being inserted.
Figure 8:
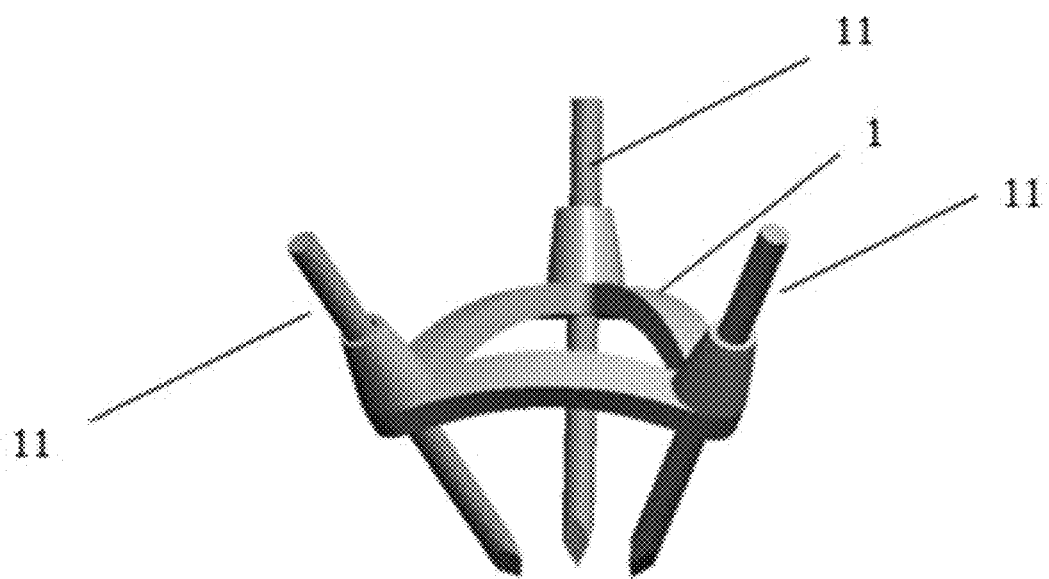
FIG. 8 depicts a perspective view of a link with three sides that has elastically returned to its first shape with all bone fastening wires inserted.
Figure 9:
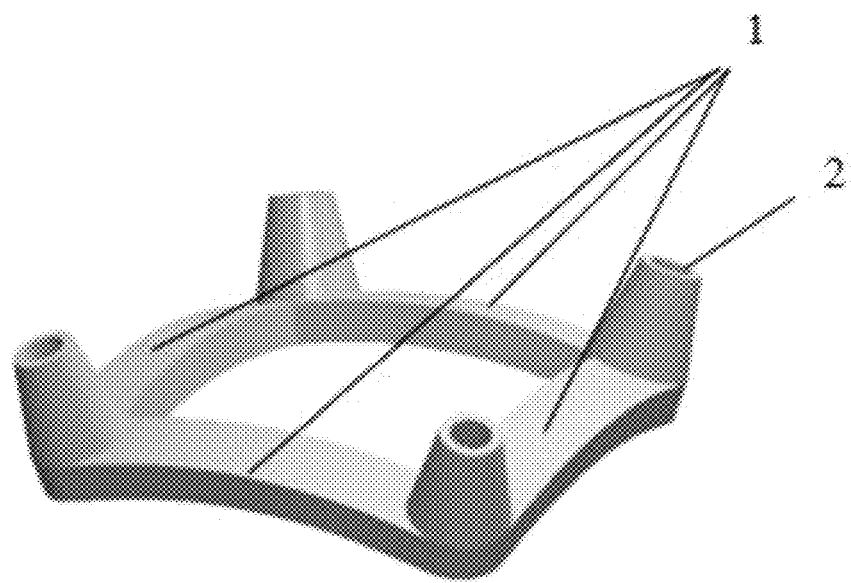
FIG. 9 depicts a perspective view of a link with four sides in its first shape having all four sides shape changing.
Figure 10:
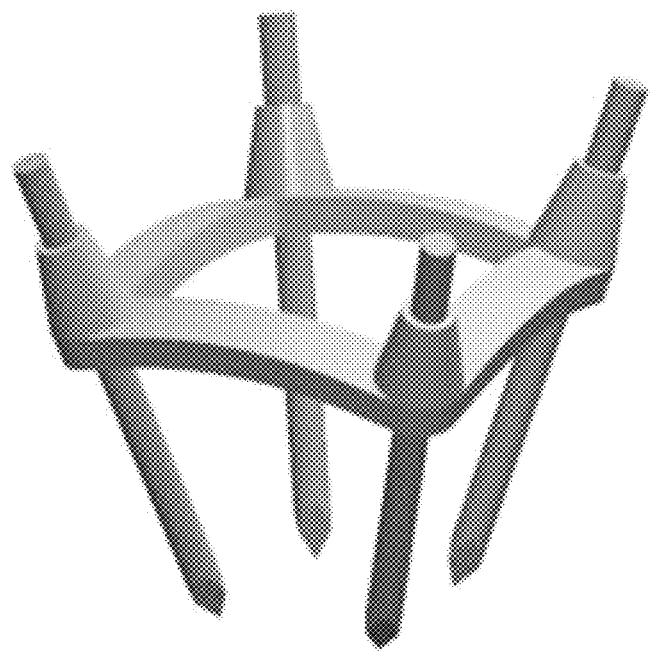
FIG. 10 depicts a perspective view of a link with four sides in its first shape after release from the instrument with all bone fastening pins inserted.
Figure 11:
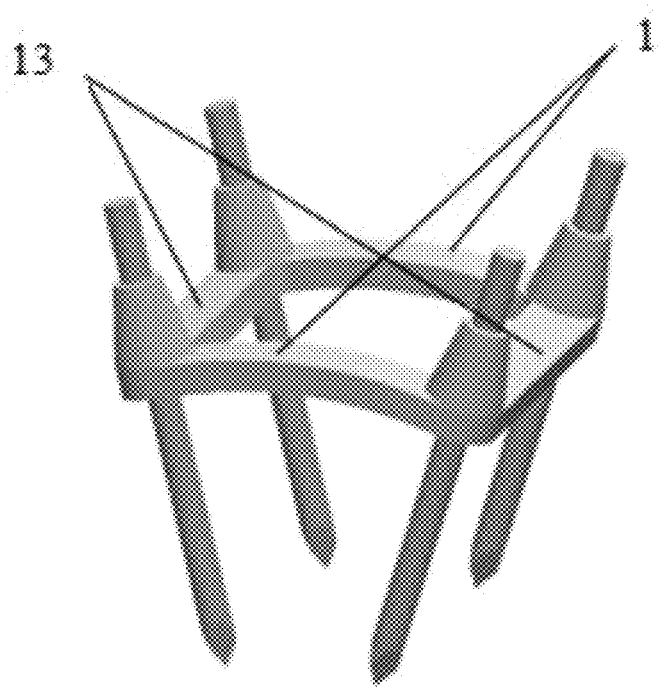
FIG. 11 depicts an orthogonal view of a link with four sides in its first shape having only two of four sides shape changing.
Figure 12:
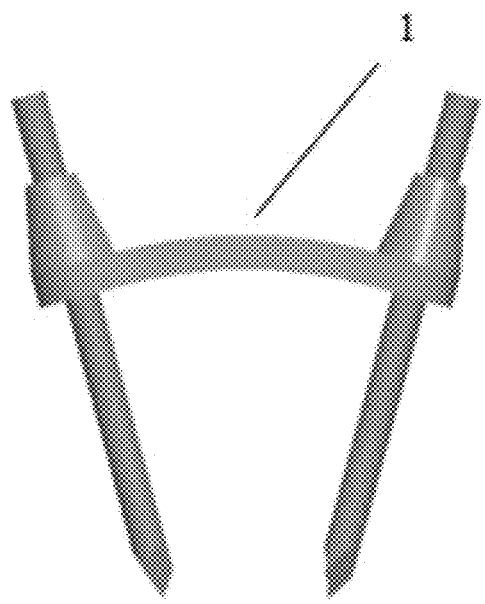
FIG. 12 depicts a perspective side view of a link with four sides in its first shape showing wire deflection with only the two shape changing sides.
Figure 13:
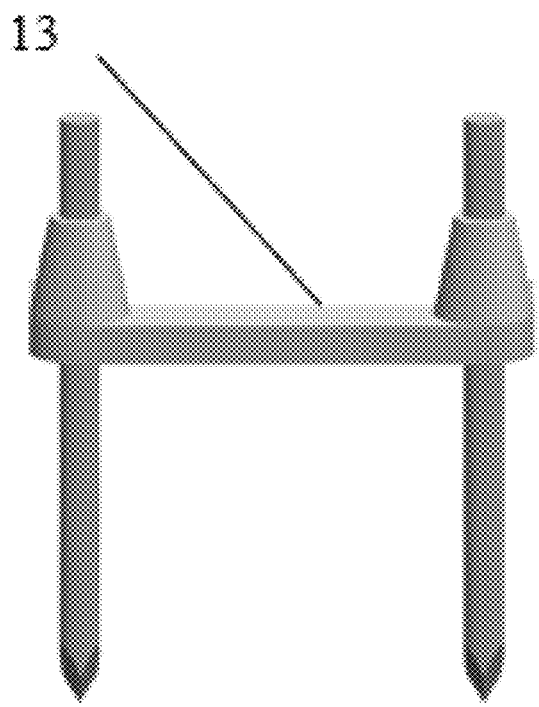
FIG. 13 depicts a link side view with four sides in its first shape showing no wire deflection for the two non-shape changing sides.
Figure 14:
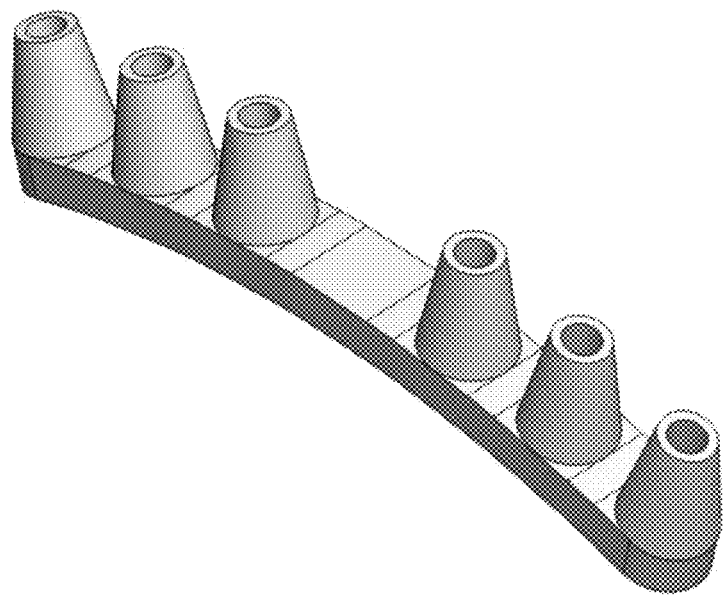
FIG. 14 depicts an orthogonal view of a link with linearly aligned pin towers.
Figure 15:
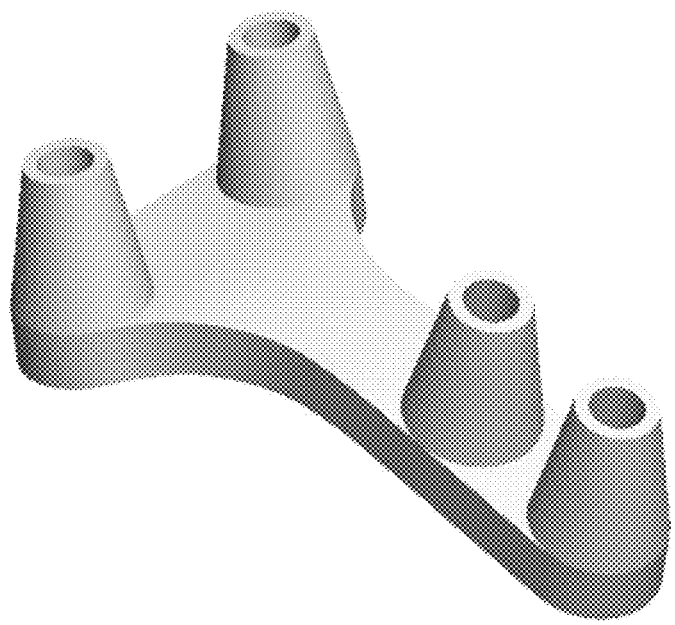
FIG. 15 depicts an orthogonal view of a link with transverse aligned pin towers.
Figure 16:
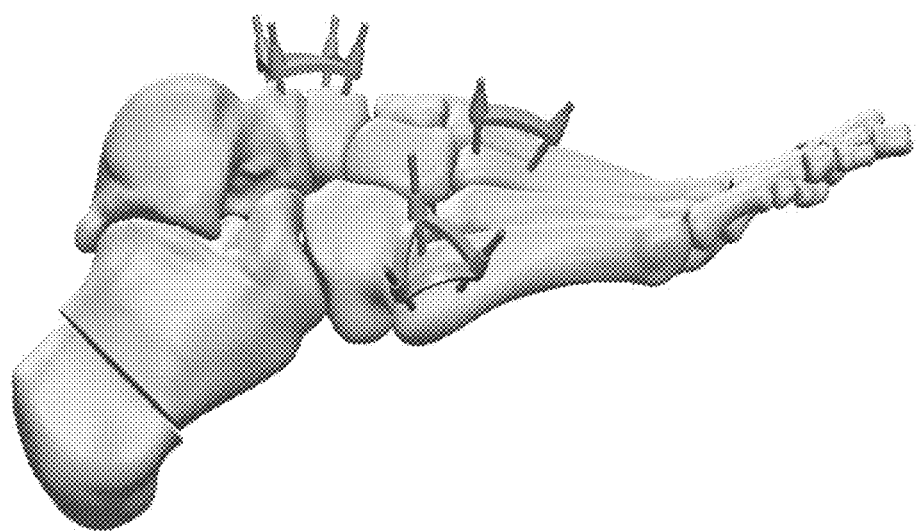
FIG. 16 depicts a perspective side view of the bones of the foot showing a two, three and four sided Link fastened through the skin and into bone.
Figure 17:
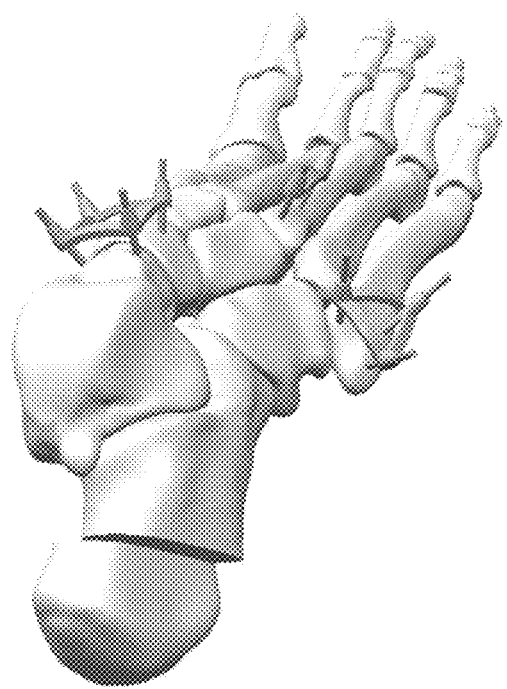
FIG. 17 depicts a perspective rear view of the bones of the foot showing a two, three and four sided link fastened through the skin and into bone.

A two pin link is shown in FIGS. 1-5. A three pin link that deflects its pins and compression to a single point is shown in FIGS. 6-8. A four pin link that deflects its pins to a single point is shown in FIGS. 9-10 and a different design shown in FIGS. 11-13 changes shape in only one direction causing two sets of pins to come together. A link with multiple linearly oriented pin towers provide surgical flexibility in where to insert the bone fixation pins and allows the surgeon to cut from the link's ends any excess length is shown in FIG. 14. A link with transverse oriented pin towers, which provide multi-axial rotational resistance to enhance fixation, is shown in FIG. 15. A side view of the bones of the foot is shown in FIG. 16 with multiple links fixated to bone. A rear view of the bones of the foot is shown in FIG. 17 with multiple links fixated to bone is shown.

Figure 18:
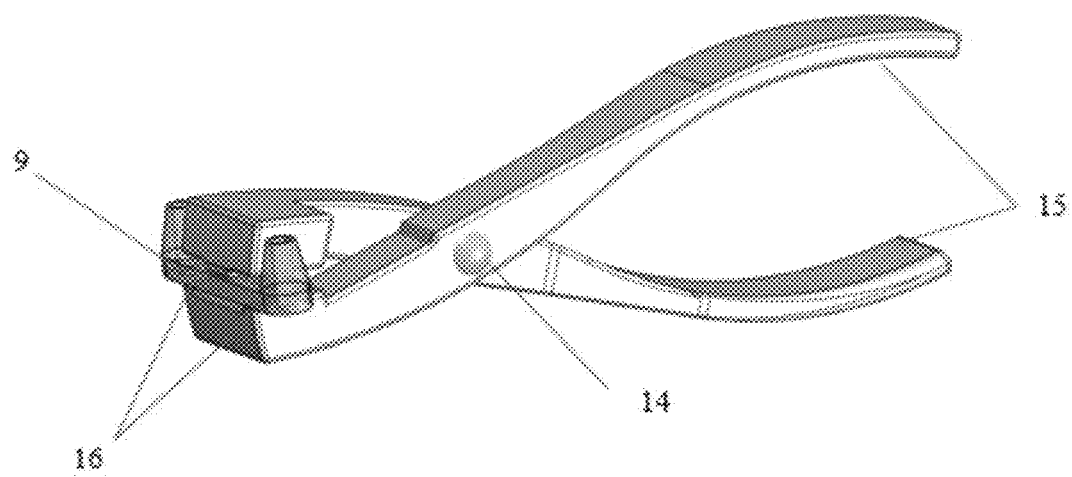
FIG. 18 depicts an illustrative example of a link being held in its stressed second shape by pliers.
Figure 19:
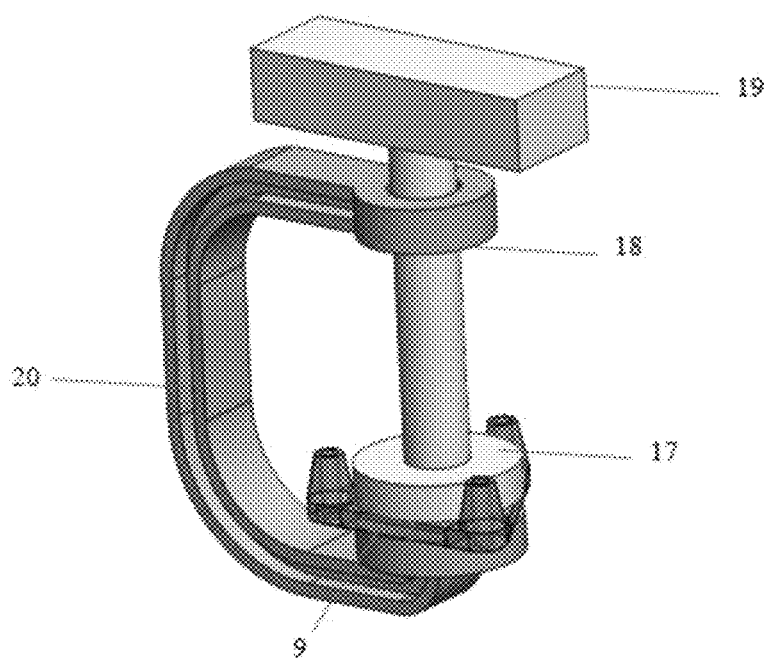
FIG. 19 depicts an illustrative example of a link being held in its stressed second shape by a compression instrument using a power screw mechanism.
Figure 20:
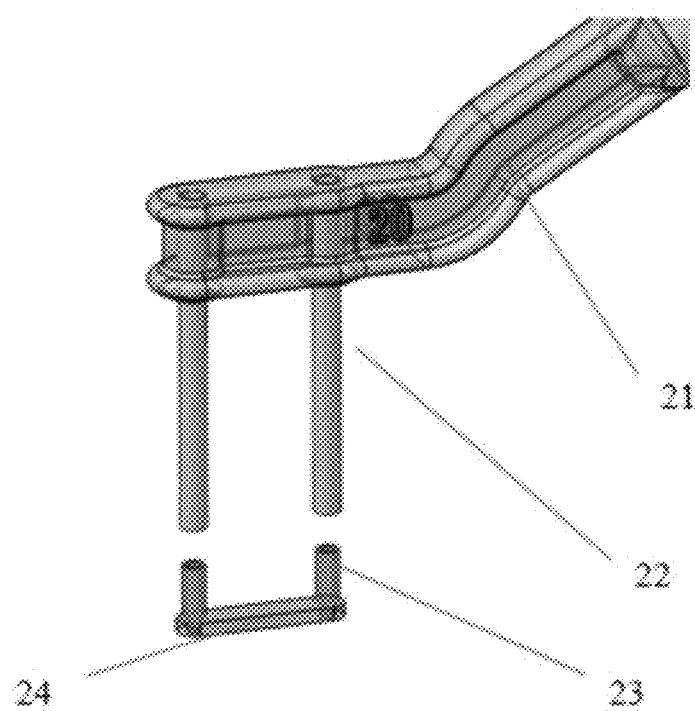
FIG. 20 depicts a perspective view of a link with cylindrical pin towers adjacent to a link instrument and drilling guide.
Figure 21:
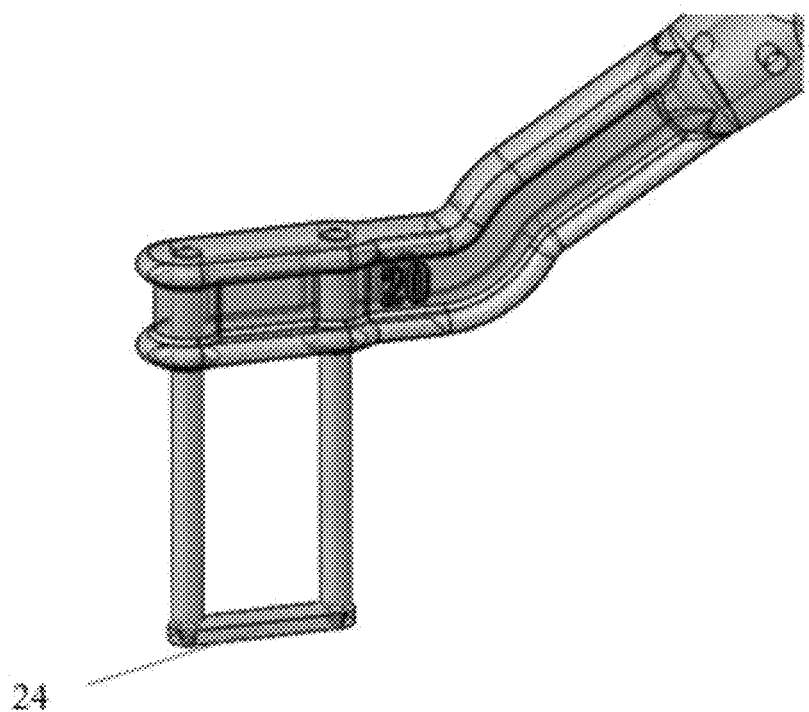
FIG. 21 depicts a perspective view of a link in its stressed second shape retained by a link instrument and drilling guide.
Figure 22:
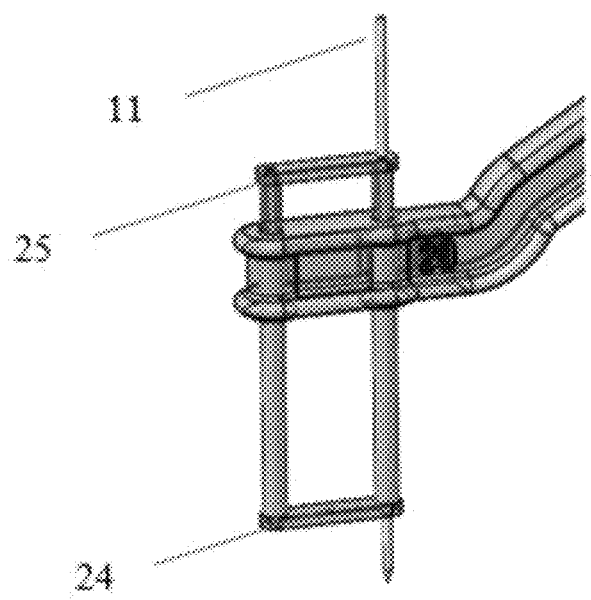
FIG. 22 depicts a perspective view of a link in its stressed second shape retained by a link instrument with an extrusion button in the up retained position.
Figure 23:
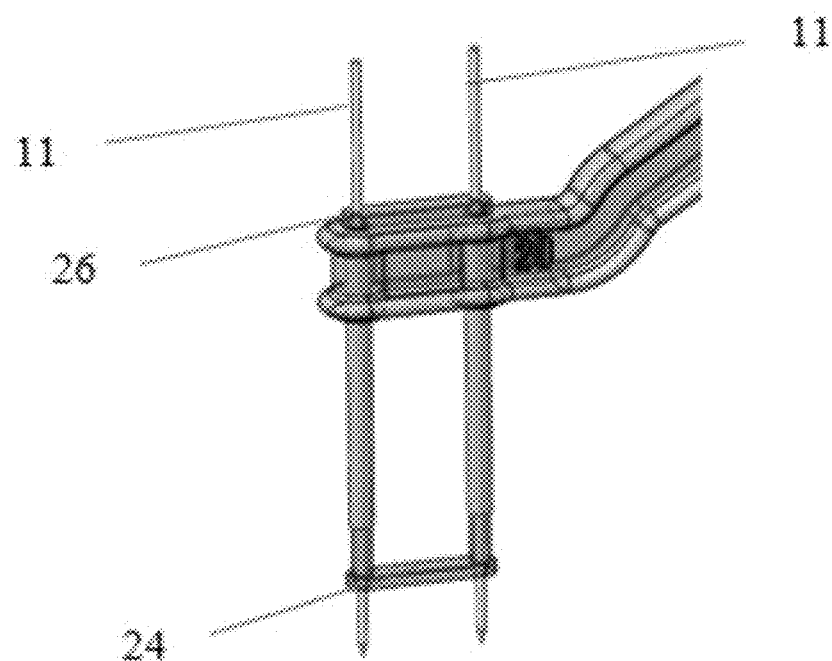
FIG. 23 depicts a perspective view of a link in its stressed second shape retained by a link instrument with an extrusion button depressed to the point just before Link release.
Figure 24:
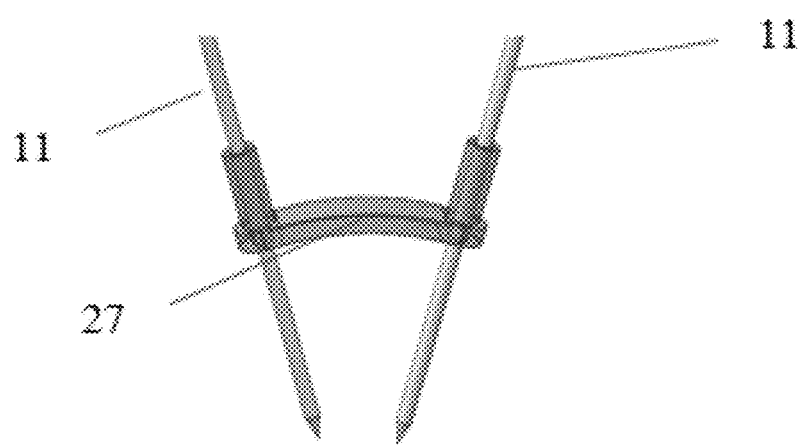
FIG. 24 depicts a perspective view of a link in its relaxed initial state acting on k-wires.

A link restraining, release and removal instrument is used to manipulate the link. All designs restrain and release while others also allow engagement with a deployed link and its removal from the pins or wires. Levers rotating about a fulcrum such as pliers can restrain, release and engage the link for removal. A plier instrument design is shown in FIG. 18. The link can be compressed into its second stressed shape using a power screw as shown in FIG. 19. The power screw actuator head can be unscrewed to release or its head turned so that it slides through the open area of the link to release the link to its unstressed state. The link can be held in its second stressed state by inserting the pin towers into tubes that maintain the alignment of the pin or k-wire holes as shown in FIGS. 20-22. A button can then be pushed to extrude the pin towers from the instrument tubes releasing the link to return to its first unstressed shape as shown in FIG. 23 to return to its unstressed first shape as shown in FIG. 24.

Figure 25:
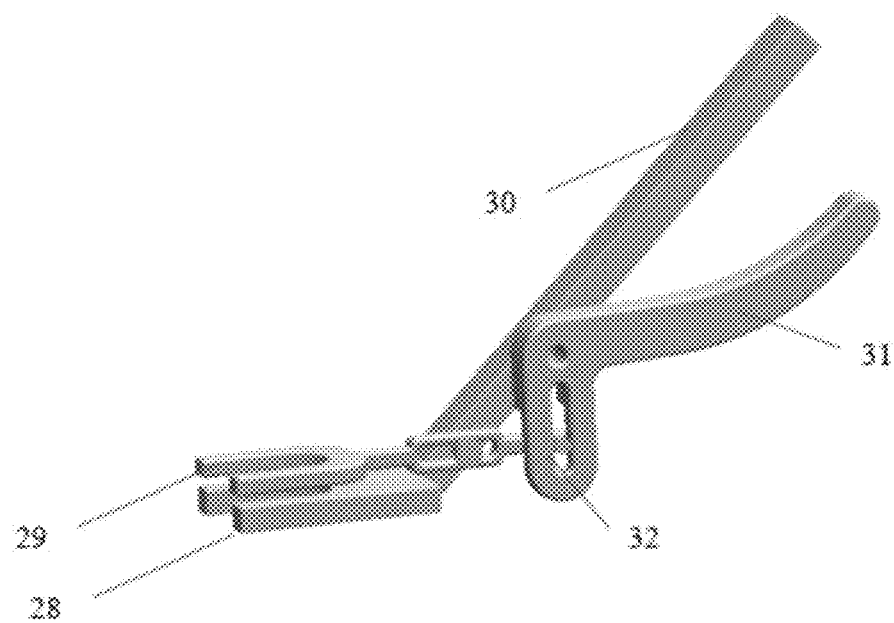
FIG. 25 depicts a perspective view of a sliding platen release instrument with fulcrum plier mechanism.
Figure 26:
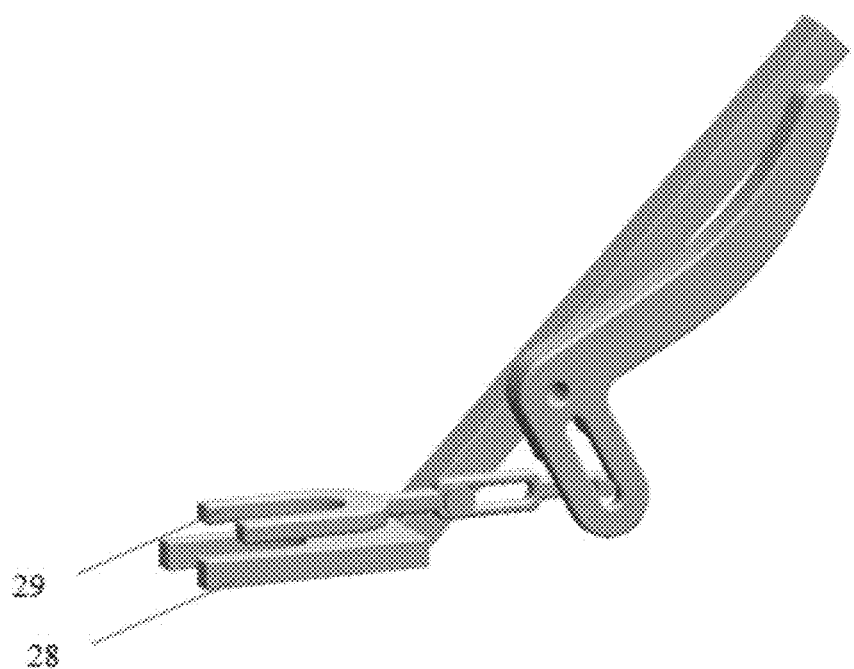
FIG. 26 depicts a perspective view of a sliding platen release instrument showing platen in release position.
Figure 27:
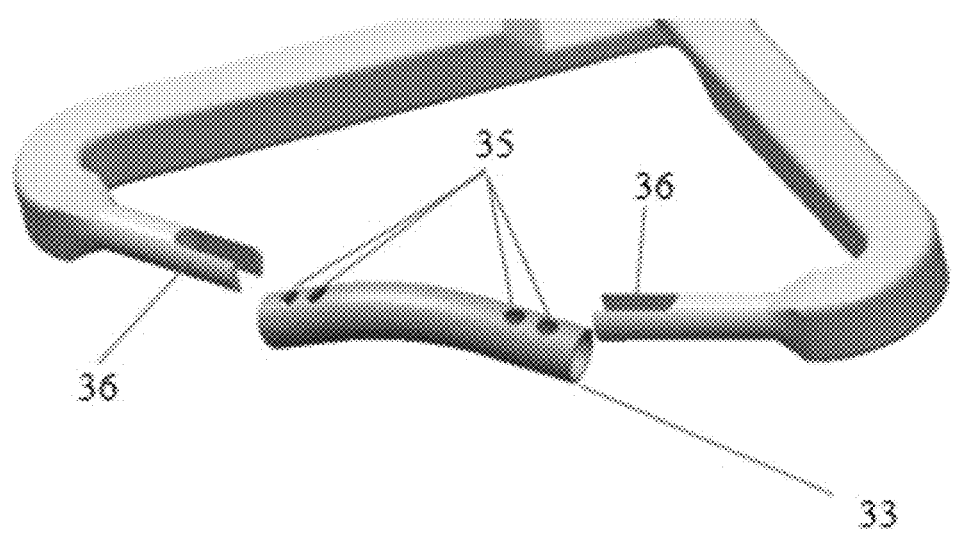
FIG. 27 depicts a perspective view of a tubular link in first shape with a plier.
Figure 28:
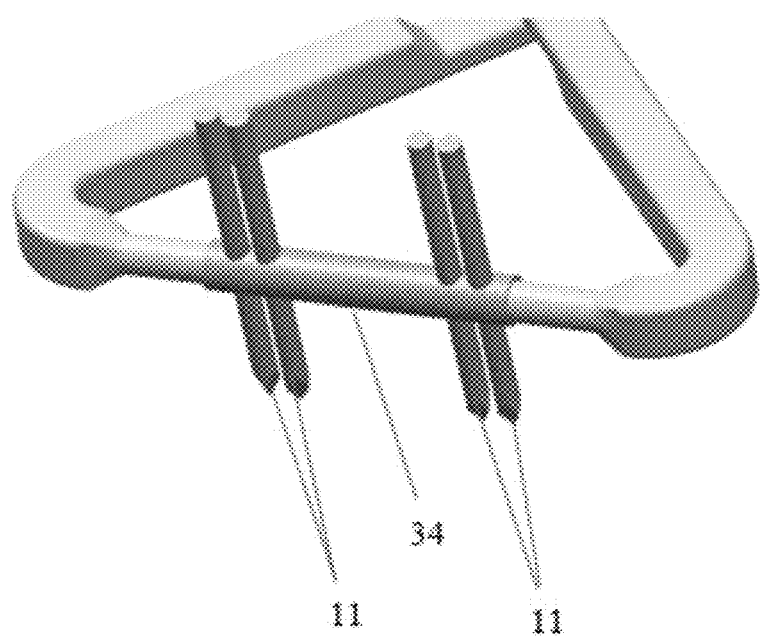
FIG. 28 depicts a perspective view of a tubular link in second stressed shape with a plier.
Figure 29:
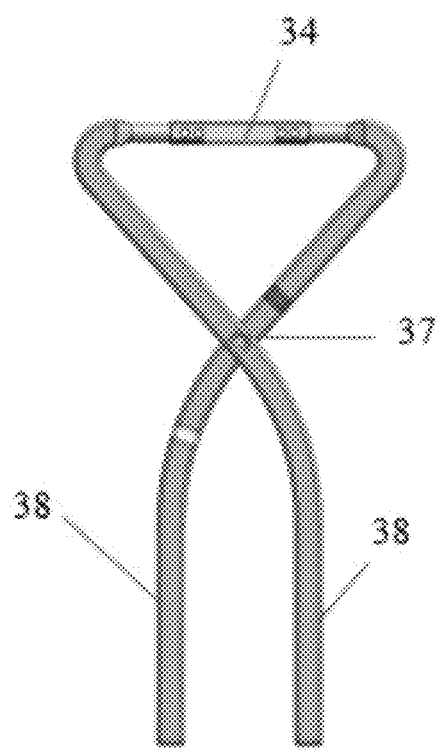
FIG. 29 depicts a perspective view of a tubular link in second stressed shape with a plier showing fulcrum point and handles.
Figure 30:
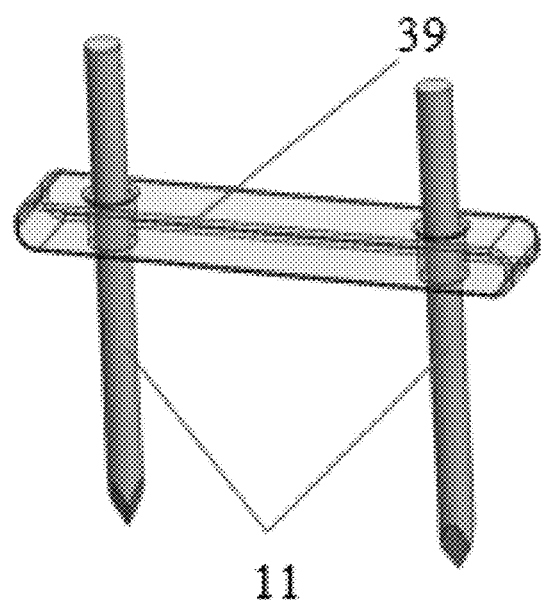
FIG. 30 depicts a perspective view of a plate link in second stressed shape with pins.
Figure 31:
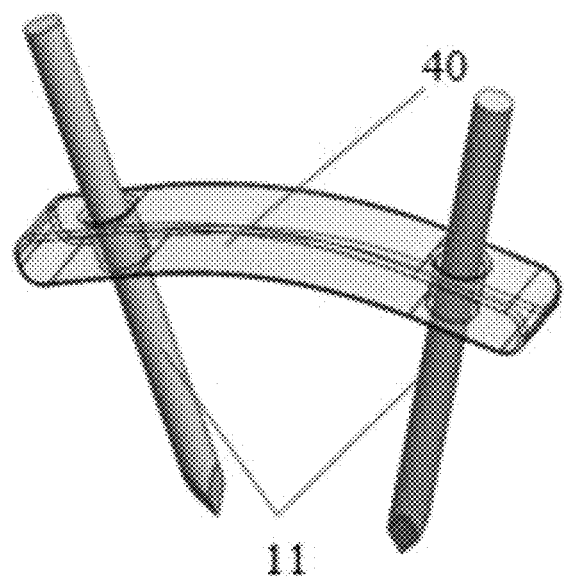
FIG. 31 depicts a perspective view of a plate link in first shape with pins.

The link can be held in its second stressed shape with a sliding head that release the link to its first shape when it is pulled away from the link as shown in FIGS. 25-26.

Links made of superelastic nitinol limit the geometry of the links that can be cost effectively fabricated. Thin plates and tubing can be cost effectively fabricated with high superelastic behavior. Nitinol links can be held in a second stressed shape with an instrument including but not limited to pliers as in FIG. 18 and FIGS. 27-29. If a tubular formed link the plier the link holder insert 36 inserts into the lumen of the tubular link to straighten the link and hold it in a second stressed shape. When actuated the pliers holder inserts swing out of the link lumen to release the link to its first shape.

Links of any design once pined to bone can be protected with a cover that protects the end of the pins and link. This cover can be fabricated of materials not limited to plastic, rubber, or latex and fastened to or stretched over the link and pins.

Although the extracorporeal bone compressing link of the present invention has been describe in connection with the shown embodiments, it is not intended to be limited to the specific forms set forth herein, but, on the contrary it is intended to cover such modifications, alternatives and equivalents as can reasonably be included within the scope and spirit of the invention as defined by the appended claims.

Additional variations of these embodiments will be obvious to those of ordinary skill in the art. Therefore, the spirit and scope of the appended claims should not be limited to the foregoing description. Only those claims specifically reciting "means for" or "step for" should be construed in the manner required under the sixth paragraph of 35 U.S.C. § 112.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. The scope of protection is not limited by the description set out above, but is only limited by the claims which follow, that scope including all equivalents of the subject matter of the claims.

Amounts and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described. The symbol "~" is the same as "approximately".

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification are to be understood as being modified in all instances by the term "about." Accordingly, unless indicated to the contrary, the numerical parameters set forth in this specification are approximations that can vary depending upon the desired properties sought to be obtained by the presently disclosed subject matter.

As used herein, the term "and/or" when used in the context of a listing of entities, refers to the entities being present singly or in combination. Thus, for example, the phrase "A, B, C, and/or D" includes A, B, C. and D individually, but also includes any and all combinations and subcombinations of A, B, C, and D.

REFERENCES

U.S. Pat. No. 10,537,370, entitled "Bone Intramedullary Fixation Scaffold," issued Jan. 21, 2020 to William Casey Fox ("Fox '370 patent").

U.S. Pat. No. 10,448,979, entitled "Shape Changing Bone Implants And Method Of Use For Enhancing Healing," issued Oct. 22, 2019 to William Casey Fox ("Fox '979 patent").

U.S. Pat. No. 10,123,831, entitled "Bone Compression Device And Method," issued Nov. 13, 2018 to Mathew P. Gephart.

What is claimed is:

1. An extracorporeal link for connecting percutaneous bone fasteners to transport, compress, or distract bone segments comprising an element wherein:
   (a) the element comprises a plurality of transverse holes, wherein
      (i) the plurality of transverse holes are located about the element, and
      (ii) each transverse hole in the plurality of transverse holes is capable of allowing a bone fastener to pass through the transverse hole in the plurality of transverse holes to secure to one or more bone segments;
   (b) the element is configured in a first configuration;
   (c) the element is operable for being held under force in a second configuration; and
   (d) the element is operable to move toward the first configuration after being released from the force, wherein (i) the movement toward the first configuration is capable of applying moments and forces to the bone fastener, and (ii) the moments and forces capable of being applied to the bone fastener are operable to act through the skin to transport and compress, or distract the one or more bone segments.

2. The extracorporeal link of claim 1, wherein the extracorporeal link is operatively positioned in a plurality of bone fragments.

3. The extracorporeal link of claim 1, wherein the material comprises one or more cross-sectional geometries.

4. The extracorporeal link of claim 1, wherein (a) each transverse hole in the plurality of transverse holes is capable of guiding the bone fastener, and (b) the bone fastener is positioned through the extracorporeal link, skin, and the bone.

5. The extracorporeal link of claim 1, wherein the movement toward the first configuration after being released from the force operatively positions the bone fastener to transport, compress or distract bone segments in at a desired direction.

6. The extracorporeal link of claim 1, wherein the extracorporeal link is in a sterile kit.

7. The extracorporeal link of claim 6, wherein the sterile kit further comprises a restraining instrument, wherein the restraining instrument comprises a restrainer selected from a group consisting of pliers, power screws, sliding platens, and pin tower tubes.

8. The extracorporeal link of claim 6, wherein the sterile kit further comprises at least one of a protective cover, a plurality of bone fasteners, and a plurality of pin tower tubes.

9. The extracorporeal link of claim 1, wherein the extracorporeal link is operatively connected to a protective cover.

10. The extracorporeal link of claim 9, wherein the protective cover comprises a material selected from a group consisting of plastic, rubber, latex, or combinations thereof.

11. An apparatus for percutaneous bone fastening comprising:

(a) an extracorporeal link, wherein (i) the extracorporeal link comprises a plurality of transverse holes, (ii) the plurality of transverse holes are located about the extracorporeal link, (iii) each transverse hole in the plurality of transverse holes is capable of allowing a bone fastener to pass through the transverse hole in the plurality of transverse holes to secure to one or more bone segments, (iv) the extracorporeal link is capable of being configured in a first configuration, and (v) the extracorporeal link is configured in a second configuration; and (b) a restraining instrument, wherein (i) the extracorporeal link is operatively positioned by the restraining instrument, (ii) the operative positioning of the instrument holds the extracorporeal link in the second configuration, and (iii) when released from the operative positioning of the restraining instrument, the extracorporeal link operably moves toward the first configuration.

12. The apparatus of claim 11, wherein the movement toward the first configuration is capable of applying moments and forces to the bone fastener.

13. The apparatus of claim 12, wherein the moments and forces capable of being applied to the bone fastener are operable to act through the skin to transport, compress, or distract the one or more bone segments.

14. The apparatus of claim 11, wherein the restraining instrument comprises a restrainer selected from a group consisting of pliers, power screws, sliding platens, and pin tower tubes.

15. A method for using an extracorporeal link for connecting percutaneous bone fasteners, the method comprising:

(a) selecting an element, wherein (i) the element comprises a plurality of transverse holes, (ii) the plurality of transverse holes are located about the element, (iii) each transverse hole in the plurality of transverse holes is capable of allowing a bone fastener to pass through the transverse hole in the plurality of transverse holes to secure to one or more bone segments, and (iv) the element is configured in a first configuration;

(b) restraining the element in a second configuration, wherein the element is restrained using external force;

(c) positioning the element near one or more bone segments;

(d) while the element is positioned and restrained, passing a plurality of bone fasteners through the plurality of transverse holes; and (e) releasing the element from the external force, wherein (i) responsive to releasing the element from the external force, the element moves toward the first configuration, (ii) the movement toward the first configuration applies moments and forces to the plurality of bone fasteners, and (iii) the moments and forces being applied to the plurality of bone fasteners act through the skin to transport, compress, or distract the one or more bone segments.

16. The method of claim 15, wherein the positioning of the element adjusts the moments and forces being applied to the plurality of bone fasteners.

17. The method of claim 15, wherein the external force is applied by a restraining instrument.

18. The method of claim 15, wherein the restraining instrument comprises a restrainer selected from a group consisting of pliers, power screws, sliding platens, and pin tower tubes.

19. A method comprising:

(a) selecting an extracorporeal link for connecting percutaneous bone fasteners comprising a material, wherein (i) the material is a material that exhibits elastic behavior, and (ii) the material is in a first configuration; and (b) restraining the material in a restraining instrument, wherein (i) the restraining instrument restrains the material in a second configuration, (ii) when restrained, the material is operable for being secured by bone fasteners to one or more bone segments;

(iii) when released from the restraining instrument, the material is operable to move toward the first configuration to transport, compress or distract the one or more bone segments.

20. The method of claim 19, wherein the material is nitinol.

21. The method of claim 19, wherein the material is stainless-steel.

22. The method of claim 19, wherein the material is titanium.

23. The method of claim 19, wherein the material is selected from the group consisting of polyethylene, polypropylene, polyester ether ketone, polytetrafluoroethylene, and nylon.

24. The method of claim 19, wherein
   (a) the material comprises memory-shape metal;
   (b) before restraining the material in the restraining instrument, cooling the material in the first configuration to at or below a first temperature, wherein
      (i) the material is operable for being reconfigured to the second configuration when at or below the first temperature;
   (c) after cooling the material and while the material is at or below the first temperature, reconfiguring the material into the second configuration, wherein
      (i) the material remains in the second configuration absent an external force at the first temperature, and
      (ii) the material is capable of moving toward the first configuration at an elevated temperature that is greater than the first temperature;
   (d) the step of restraining the material in the restraining instrument comprises
      (i) restraining the material while the materials is at or below the first temperature, and
      (ii) elevating the temperature of the material to the elevated temperature, wherein the restraining instrument restrains the material from moving from the second configuration toward the first configuration.

25. The method of claim 24, wherein the material is nitinol.

* * * * *